United States Patent [19]

Murtha et al.

[11] 4,329,531
[45] May 11, 1982

[54] HYDROALKYLATION CATALYST AND METHODS FOR PRODUCING AND EMPLOYING SAME

[75] Inventors: Timothy P. Murtha; Ernest A. Zuech, both of Bartlesville, Okla.

[73] Assignee: Phillips Petroleum Company, Bartlesville, Okla.

[21] Appl. No.: 154,548

[22] Filed: May 29, 1980

[51] Int. Cl.$^3$ ............................................. C07C 5/12
[52] U.S. Cl. .................................... 585/268; 585/425
[58] Field of Search ................................ 585/268, 425

[56] References Cited

U.S. PATENT DOCUMENTS 3,839,477 10/1974 Suggitt et al. ..................... 585/425
4,118,434 10/1978 Murtha et al. ..................... 585/268

Primary Examiner—Curtis R. Davis

[57] ABSTRACT

An aromatic hydrocarbon is contacted under suitable hydroalkylation conditions with a composition comprising a calcined, acidic, nickel and rare earth-treated crystalline zeolite.

22 Claims, No Drawings

HYDROALKYLATION CATALYST AND METHODS FOR PRODUCING AND EMPLOYING SAME

The invention relates to the hydroalkylation of hydrocarbons.

Prior art catalysts and processes in the field of hydroalkylation suffer from several drawbacks. The support materials for certain catalysts are not able to withstand the temperatures employed in a typical air burn-off regeneration operation. Such regeneration operations are commonplace in the catalytic art for hydrocarbon conversions of various types and it is highly desirable that a catalyst used for a hydroalkylation process be stable to such typically employed regeneration conditions. Also, productivity is rather low as judged by the low liquid hourly space velocities (LHSV) that are utilized in the prior art. Thus a process employing a more active and more selective hydroalkylation catalyst is desired. Furthermore, a number of the catalysts of the prior art used in hydroalkylation processes are prepared by very complex and time consuming processes. For example, starting with a powdered crystalline zeolite support, the support is cation exchanged, washed and then incorporated into a matrix of another material such as silica-alumina. This combination is calcined, cooled, and impregnated with certain metal salts. Finally the composite is extruded into pellets and the like. Thus it is desirable to develop a process employing a catalyst that is easier and cheaper to produce. Frequently, catalysts of the prior art used in a hydroalkylation reaction were of fixed acidity because of the type of support material utilized. This left little variation that could be made in this important property of the hydroalkylation catalyst. Catalysts which are easily varied in their acidity characteristics are extremely desirable. In some prior art processes the catalyst employed has a relatively short life. It is therefore desirable to develop a hydroalkylation process in which the catalyst is effective over a long period of time. Some hydroalkylation processes of the prior art require that the hydrocarbon feed stream be essentially free of oxygen or oxygen-forming materials such as water. Because it is costly to remove water or other oxygen sources from the hydrocarbon feed stream, it is desirable to develop a hydroalkylation process in which at least small quantities of water or other oxygen sources can be present without detrimental effects.

OBJECTS OF THE INVENTION

An object of the present invention is to provide a hydroalkylation catalyst and a method for its production.

Another object of the present invention is the hydroalkylation of aromatic compounds in which most if not all of the above described problems with prior art catalysts and processes are eliminated or at least minimized.

Another object of the invention is a process for the hydroalkylation of aromatic compounds in which the presence of small amounts of water can be tolerated.

Another object of the invention is a hydroalkylation process which employs a catalyst having a longer active life than prior art catalysts.

Another object of the invention is a hydroalkylation process using a catalyst which retains its activity and selectivity longer in the presence of small amounts of water than prior art catalysts.

SUMMARY

According to the invention, there is provided a calcined, acidic, nickel and rare earth-treated crystalline zeolite, a method for its production, and a hydroalkylation process which employs it.

DETAILED DESCRIPTION OF THE INVENTION

The catalyst composition of the present invention can be briefly described as an acidic, calcined, nickel and rare earth exchanged crystalline zeolite. The catalyst is highly active and selective for hydroalkylation for long periods of time and is stable to catalyst regeneration conditions. The activity or selectivity of the catalyst for hydroalkylation can be further improved by carrying out the calcination step at a moderate temperature in the range of from about 150°–400° C., and/or by contacting it with a halide source for activation. The useful life of the catalyst for hydroalkylation can be prolonged by contact with water and/or a halide source.

The support material employed in the instant invention is a crystalline zeolite which has been cation exchanged with rare earth, nickel and ammonium cations. Some of the more commonly employed crystalline zeolites which are suitable for use in accordance with the present invention are those having a pore diameter within the range of from about 7 to about 12 angstroms. For example some of the more commonly known and used crystalline zeolites having a pore diameter within this range are the Type L, Type X and Type Y crystalline zeolites. Crystalline zeolites are sometimes called molecular sieves as known in the art because of their essentially uniform pore diameters. Some suitable Type Y synthetic crystalline zeolites are described for example in U.S. Pat. No. 3,130,007, some suitable Type X zeolites are described in U.S. Pat. No. 2,882,244 and some suitable Type L zeolites are described in U.S. Pat. No. 3,216,789. Such materials are presently commercially available as for example zeolites SK-40 (Type Y) 13X (Type X) and SK-45 (Type L) from the Linde Division of Union Carbide Corporation, New York, N.Y.

The zeolite is treated under cation exchange conditions in accordance with the invention with rare earth, nickel and ammonium compounds in order to provide a suitable support material for use in the invention. Generally the cationic metal removed from the crystalline zeolite by the cation exchange process is an alkali metal, usually sodium. The alkali metal is sufficiently removed by cation exchange so that the remaining alkali metal content after the cation exchange step is within a range of from about 0.01 to about 2 percent by weight zeolite. Based on the runs carried out in accordance with the invention and reported herein it is believed that good results can be obtained when the alkali metal content of the cation exchanged zeolite is within a range of from about 0.1 to about 1 percent by weight zeolite.

It is convenient in accordance with the invention to treat the zeolite with a cation exchange solution containing more than one of the cations to be exchanged with the alkali metal cation of the zeolite. For example the crystalline zeolite can be treated one or more times with a cation exchange solution comprising nickel, rare earth and ammonium cations. Alternatively, each cation can be in a separate solution and the zeolite is treated with each solution one or more times. Other variations in the cation exchange process can be used. The only requirement is that the zeolite be treated under cation exchange conditions with nickel, rare earth and ammonium cations.

It is contemplated that any of the readily available rare earth metal compounds can be employed in the cation exchange solution. The compounds used are those in which the rare earth metal-containing ion is present in the cationic state. Representative rare earth metal compounds include nitrates, bromides, acetates, chlorides, iodides, sulfates and mixtures thereof of one or more of the rare earth metals including cerium, lanthanum, praseodymium, neodymium, samarium, europium, gadolinium, terbium, dysprosium, holmium, erbium, thulium, ytterbium, and lutetium. Compounds of the rare earths named above may be employed singly, however, it is often convenient to employ mixtures of the rare earths as these are commercially available. For example, mixtures of rare earth metal compounds such as the chlorides of lanthanum, cerium, praseodymium, neodymium, samarium and gadolinium are available commercially at a relatively low cost and may be effectively employed.

The concentration of rare earth compounds in the aqueous exchange solution and the exchange conditions employed can be varied over a wide range to produce an ion exchanged crystalline zeolite with a rare earth content selected over a broad range. Generally, the content of the final catalyst composite in terms of the rare earth elements is from about 2 to about 25 weight percent. Based on the results of the runs described herein it is believed that a rare earth content within the range of from 5 to 20 weight percent of the final catalyst composite is often advantageous. Good results were obtained when employing a catalyst having a rare earth content of about 10 percent by weight of the final catalyst composite.

As noted above, it is advantageous to cation exchange the zeolite material with a mixture of rare earth, nickel and ammonium compounds. Any convenient ammonium compound may be employed although the chloride is preferred because it is inexpensive and readily available. The weight ratio of ammonium compound to nickel and rare earth compounds in the aqueous exchange solution can be selected over a broad range. Generally the weight ratio of ammonium compound to nickel and rare earth compounds combined is within the range of from about 0.05:1 to about 20:1, although based on the data contained herein it is estimated that a range of from about 0.2:1 to about 5:1 can be used with good results.

The nickel compounds which are employed with the above-named rare earth metal compounds and ammonium compounds are those wherein the nickel ion is present in the cationic state. Some compounds representative of the nickel compounds suitable for use in the invention include the nitrates, bromides, acetates, chlorides, iodides and sulfates of nickel and mixtures of any two or more thereof.

The nickel content in the final composition can also be selected over a broad range. Generally the composition will comprise from about 0.1 to about 20 weight percent nickel based on weight of the final composition, although the runs carried out in accordance with the invention and described herein indicate that good results can be obtained employing a nickel content within a range of from about 1 to about 10 percent by weight based on weight of the final composition.

The cation exchange process can be carried out in a batch or continuous fashion. Generally the exchange process is carried out on a continuous basis. Good results were obtained employing the following typical conditions. A fixed bed of the zeolite material is treated with an aqueous solution of the rare earth, nickel and ammonium compounds at a temperature of from about 90° C. to about 110° C. under conditions such that from about 0.1 to about 0.5 of the volume of aqueous salts solution per volume of zeolite is contacted with the zeolite per hour or, in other words, an LHSV ranging from about 0.1 to about 0.5 is employed in the exchange process. Under these conditions, the exchange process can be completed in 48 hours or less to achieve the desired level or rare earth, nickel and ammonium ions in the zeolite. The exchanged zeolite is then washed free of excess ions with water. The wash water is removed by drying the zeolite at a temperature ranging from about 100° C. to about 300° C. prior to calcination.

The calcination of the catalysts of the instant invention is carried out in the presence of air within a broad temperature range of from about 150° C. to about 400° C. and preferably from about 175° C. to about 325° C. within a time period which ranges broadly from about 1 hour to about 24 hours and preferably from about 2 to about 5 hours. It is believed to be especially important in order to obtain highly desirable catalyst activity that the upper temperature limit in the calcination step not be exceeded.

A calcination procedure found to be effective is to heat the catalyst in a stepwise manner at a temperature within a range of from about 175° C. to about 225° C. for a period of time within a range of from about 1 to about 2 hours and then at a temperature within a range of from about 275° C. to about 325° C. for a period of time within a range of from about 1 to about 2 hours.

The hydroalkylation catalysts can be modified with a halide source compound according to the instant invention prior to or simultaneous with its use by simply contacting the halide source with the catalyst.

The amount of the halide contacted with the catalyst is an important aspect of the present invention because too much halide will poison the catalyst whereas too little halide will not improve the selectivity of the catalyst to produce the desired hydrocarbon. Thus, the halide source is contacted with the catalyst in an amount sufficient to improve the selectivity of the catalyst composition to produce the desired product. The halide employed can be selected from, for example, fluorides, chlorides, bromides and iodides.

The halide treatment to improve selectivity can be conducted by a single treatment of the catalyst with the halide compound or by adding a suitable halide compound to the hydrocarbon feedstream. In the instant invention when a single treatment procedure is utilized, the amount of halide ion employed is broadly within the range of from about 0.01 up to about 10 milligrams of halide ion per gram of catalyst and preferably from about 0.1 to about 4 milligrams of halide ion per gram of catalyst. If the continuous treatment is utilized in the instant invention, the broad range of halide compound utilization is from about 0.01 up to about 5 milligrams of halide ion per gram of catalyst and preferably from about 0.1 up to about 2 milligrams of halide ion per gram of catalyst. It is presently believed that the halogen component of a catalyst treated with a halide source as above described exists in the halide form and thus is referred to herein as a halide, but the exact form of the halogen component of the catalyst has not been investigated and is not to be a limitation on the invention.

Some suitable sources of halide used to treat the catalyst according to the instant invention include the elemental halogens themselves such as fluorine, bromine, chlorine or iodine and the hydrohalides of said elements (HF, HBr, HCl and HI). Because use of the above halide sources generally requires careful control of the addition, it is preferred to employ organic compounds as a halide source in the instant invention. A wide variety of halogen-containing organic compounds can be employed to provide halide for use in the instant invention. These compounds can contain one or more atoms of fluorine, bromine, chlorine or iodine or mixtures thereof per molecule and the carbon content of such compounds is generally in the range of from 1 to 4 carbon atoms per molecule. For example, such compounds include alkyl halides, acid halides, or fully halogenated carbon compounds such as carbon tetrachloride or tetrachloroethylene and the like. Examples of other suitable organic compounds which can be employed as a halide source include chloroform, bromoform, dichloromethane, dibromomethane, difluoromethane, chloromethane, bromomethane, 1,4-dichlorobutane, 1,4-dibromobutane, 1-chlorobutane, 1-fluorobutane, 1-bromobutane, 1,2-dichloroethane, 1,2-dibromoethane, 2-chloropropane, 2-bromopropane, acetyl chloride, acetyl iodide, acetyl bromide, bromochloromethane, 1-bromo-4-chlorobutane, 1,2-dichloroethylene, 1,2-dibromoethylene and mixtures thereof. From the results of the runs disclosed herein, it is believed that organic compounds containing chlorine or bromine will produce the best results and thus such compounds are preferred.

The procedure in which the halide source is added to the aromatic hydrocarbon feed stream can be utilized when the catalyst is fresh, i.e., previously unused, or said procedure can be utilized after one or more regenerations of the above-mentioned catalyst. As most of the runs described herein indicate, a fresh catalyst is improved somewhat by regeneration and in many cases it may be desirable to subject a fresh catalyst to the regeneration process prior to using it.

Although the source of halide used to modify the catalyst of the invention can be added to the hydrocarbon feed in one portion, good results were obtained by adding the halide source to the feed over a period of time, generally from about 1 to about 3 hours although longer times can be employed. It is belived that a more efficient utilization of the halide source is achieved by the above-described gradual addition of said halide source to the catalyst, such as when that halide source is added to the hydrocarbon feed, but in some instances a shorter catalyst modification time may be more desirable and produce an equal or superior catalyst.

The catalyst used in the instant invention can be readily regenerated by heating the catalyst in the presence of flowing air for a suitable time period at an elevated temperature such as a temperature within a range of from about 450° C. to about 550° C. It is desirable to then cool the catalyst in the presence of flowing inert gas such as nitrogen and then reduce it under hydrogen. It is surprising that the instant catalysts can be regenerated at such high temperatures when as noted above the use of such a high calcination temperature when making the catalyst would result in a rather inactive and/or nonselective catalyst for hydroalkylation.

The composition described above is employed for the hydroalkylation of aromatic hydrocarbons to produce cycloalkyl aromatic hydrocarbons. Some of the feedstocks which are suitable for use in the present invention are aromatic compounds, i.e., monocyclic aromatic hydrocarbons and alkyl-substituted monocyclic aromatic hydrocarbons. Some specific examples of these are benzene, toluene, xylenes, and the like, and mixtures thereof. The aromatic hydrocarbon feedstocks should be essentially free of sulfur-containing compounds and other known poisons for hydrogenation catalysts in general. However, it is believed that a small amount of water in the feedstock is beneficial for maintaining catalyst activity over an extended period, e.g., several days.

While the presence of too much water can adversely affect the activity of the catalyst used in the present inventive process, the amount of water that can be present varies over a substantial range. The amount of water present in the reaction zone, expressed as ppm by weight in the feedstock, when using the inventive process should be an amount effective to preserve and maintain the activity of the catalyst for as long as reasonably possible. Generally the amount of water present in the feedstock is within the range of from about 5 to about 500 parts per million, although a range of from about 10 to about 100 parts per million is more often used because the activity of the catalyst is better maintained. The most preferred range of water content is from about 20 to about 50 parts per million as a water content within this range effectively eliminates any adverse effects on the catalyst activity due to the presence of water and is beneficial in maintaining the activity of the catalyst. Many suitable feedstocks that are available contain water in a suitable amount to supply the desired amount to the reaction zone. However, the feedstock may be treated to reduce or increase the water content as may be required. Though generally less convenient, water may be added to the reaction zone as a separate stream.

The invention is particularly valuable for the conversion of benzene to cyclohexylbenzene. Cyclohexylbenzene is known as a valuable solvent and chemical intermediate. It can be converted in high yield to phenol and cyclohexanone by autooxidation with subsequent acid treatment. It is also useful as an intermediate in the production of cyclohexene which in turn can be utilized for the production of adipic acid and caprolactam.

The aromatic hydrocarbon feedstock is fed to the catalyst in a reaction zone operated under hydroalkylation conditions which can vary widely. The feedstock liquid hourly space velocity (LHSV), reaction temperature and pressure, and the hydrogen feed rate are not particularly critical. The liquid hourly space velocity (LHSV) generally ranges from about 1 to about 100, the reaction pressure generally ranges from about 690 to about 13,800 kPa (about 100 to about 2,000 psig), the hydrogen feed rate generally ranges from about 0.2 to about 1 mole per mole of aromatic hydrocarbon feedstock per hour, and the reaction temperature generally ranges from about 100 to about 250° C. Based upon the runs described herein good results can be obtained employed a liquid hourly space velocity (LHSV) within the range of from about 5 to about 25, a reaction pressure within the range of from about 1,380 to about 6,900 kPa (about 200 to about 1,000 psig), a hydrogen feed rate within the range of from about 0.2 to about 1 mole per mole of aromatic hydrocarbon feed per hour, and a reaction temperature within the range of from about 165 to about 225° C.

The hydroalkylation reaction is conveniently carried out by having the above described catalyst in a fixed bed reactor and then contacting said catalyst with the aromatic hydrocarbon feed and hydrogen in an upflow or downflow arrangement. It is also possible to employ a countercurrent flow of hydrogen and the aromatic hydrocarbon feed over the catalyst in the reaction zone. It is also possible to carry out the hydroalkylation reaction under batch conditions although a batch process is less preferred, because it is normally more expensive to operate and initial equipment costs are higher based upon the same size process.

Although a fixed bed catalyst is mentioned above, most any type of reaction zone can be used as the particular type of reaction zone is not believed to be a critical parameter of the invention.

A typical regeneration procedure for the above-described catalyst includes purging the system of hydrogen with an inert gas such as nitrogen, then allowing air to enter the reaction zone and heating the catalyst to a temperature within a range of from about 450° to about 550° C. in the presence of flowing air and maintaining the temperature of the catalyst within said range in the presence of flowing air for a suitable period of time, which is generally within a range of from about 1.5 to about 4 hours. The catalyst is then cooled with a suitable gas, such as air or nitrogen at a temperature of about 200° C. and is then reduced with hydrogen for a period of about 0.5 to 1 hour. After the catalyst has cooled to the desired reaction temperature, it is ready for use such as in a hydroalkylation reaction. Generally, it is desirable to retreat the catalyst with the halide source after each regeneration process to insure that the catalyst will provide the highest selectivity to the desired cycloalkyl aromatic compound.

The reaction mixture from the reaction zone can usually be conveniently separated into the desired components by simple fractional distillation, and recycle of the unreacted feedstock and unreacted hydrogen can be accomplished as desired. The hydroalkylation products can be further purified as desired after separation from unreacted feedstock.

EXAMPLE 1

Five catalysts were prepared for use in hydroalkylation reactions. These catalysts were all calcined at a temperature above the preferred range utilized for the catalysts of this invention and in one instance, (catalyst No. 1) did not contain rare earth metals as part of the catalyst component.

The catalysts of this example were all based upon a type X crystalline zeolite (Davison 13X mole sieves). The crystalline zeolite material of type X was treated under cation exchange conditions with aqueous solutions of compounds described in more detail below. The cation exchange reaction was carried out in a glass tube of 45 millimeter diameter which was equipped with heating means and means for passing an aqueous solution of compounds therethrough. Ammonium chloride was utilized as the source of ammonium ions in the cation exchange solution while nickel chloride hexahydrate was the source of the nickel ions in the cation exchange solution and when utilized a mixture of rare earth chlorides was the source of the rare earth metals in the cation exchange solution. Said rare earth chlorides were obtained from the American Potash Corporation and had the following composition:

$MCl_3 \cdot 6H_2O$ wherein M equals lanthanum 23%, cerium 43.5%, praseodymium 5.4%, neodymium 17.9%, samarium 1.9%, gadolinium 0.6%, and others 0.2%.

Catalyst No. 1 was prepared such that it contained no rare earths. In the preparation of this catalyst, 200 grams of a type X crystalline zeolite was wetted with a portion of a solution of 400 grams of ammonium chloride and 200 grams of nickel chloride hexahydrate in 4 liters of distilled water and then charged to the cation exchange reactor described above. The remainder of the solution of ammonium chloride and nickel chloride was then pumped over the zeolite bed at an LHSV of about 0.25 at a temperature of about 95°–100° C. The zeolite material was cooled, filtered and then washed six times with 350 mL portions of water and allowed to dry in air overnight. The zeolite material was then calcined by heating overnight in air to about 218° C. (425° F.) and then increasing the temperature over an 8 hour perior to 532° C. (990° F.) and then allowed to cool. This catalyst (No. 1) contained 7.7% nickel and 1.54% sodium.

The other catalysts for the runs of this example were prepared in a similar manner to that described for the preparation of catalyst no. 1 except aqueous solutions of ammonium chloride, nickel chloride hexahydrate and the mixed rare earth chlorides were utilized in the cation exchange step. Variation in the concentration of the components of the cation exchange solution were utilized to obtain catalysts of varying nickel, rare earth and sodium content. For example, catalyst No. 4 was prepared by charging 200 grams of a type X crystalline zeolite (Davison 13X mole sieves of 8-12 mesh) to the cation exchange reactor described above. An aqueous solution of 400 grams of ammonium chloride, 100 grams of mixed rare earth chlorides previously described, and 200 grams of nickel chloride hexahydrate in 4 liters of deionized water was prepared. The crystalline zeolite material was first wetted with a portion of the above solution and then charged to the cation exchange reactor and the remainder of the aqueous solution pumped over the crystalline zeolite at an LHSV of about 0.25. The temperature in the cation exchange zone was about 100° C. After the solution had been pumped through the crystalline zeolite bed, the material was cooled, filtered and washed six times with 350 mL portions of water and then allowed to dry in ambient air. This material was then calcined by heating overnight in the presence of air in a furnace to about 216° C. (420° F.) and then the temperature increased slowly up to about 500° C. (932° F.) over an 8 hour period and then allowed to cool in air. The catalyst (No. 4) thus prepared contained 4.68% nickel, 9.5% rare earths and 0.63% sodium.

Catalyst Nos. 2, 3 and 5 were also calcined at about 500° C. in the same manner as that described for catalyst No. 4. A summary of the properties of catalyst Nos. 1 through 5 is presented in Table I below.

TABLE I

| Catalyst No. | Calcination Temp., °C. | Weight Per Cent | | | | | | | |
|---|---|---|---|---|---|---|---|---|---|
| | | Na | Ni | La | Ce | Pr | Nd | Sm | Gd |
| 1 | 532 | 1.54 | 7.7 | — | — | — | — | — | — |
| 2 | 500 | 0.98 | 2.1 | 3.6 | 5.6 | 0.64 | 2.5 | 0.13 | 0.02 |

TABLE I-continued

| Catalyst No. | Calcination Temp., °C. | Weight Per Cent | | | | | | | |
|---|---|---|---|---|---|---|---|---|---|
| | | Na | Ni | La | Ce | Pr | Nd | Sm | Gd |
| 3 | 500 | 0.22 | 2.5 | | | 11.5(est.)[a] | | | |
| 4 | 500 | 0.63 | 4.68 | 2.7 | 4.4 | 0.52 | 1.8 | 0.08 | 0.02 |
| 5 | 500 | 0.72 | 6.5 | | | 7.5(est.)[a] | | | |

[a] Estimated total rare earth content.

The catalysts described above in Table I were utilized in the hydroalkylation of benzene. In these hydroalkylation runs, a small tubular reactor equipped for continuous reaction operation was charged with the catalytic material. The catalyst in each instance was prereduced at 400°–500° C. under 3,450 kPa (500 psig) hydrogen at a flow rate of 0.32 liters per minute of hydrogen for a period of 2 to 4 hours. However, Catalyst No. 5 was prereduced at 300° C. for a period of 1.5 hours. During each benzene hydroalkylation run, the hydrogen pressure was maintained at 3,450 kPa (500 psig) and at a flow rate of 0.32 liters per minute of hydrogen during the time in which samples were withdrawn from the reactor effluent for analysis by gas-liquid phase chromatography. The benzene feed was believed to contain water at a concentration of between 25 and 100 ppm. Other reaction conditions and the results obtained in the hydroalkylation runs are shown below in Table II.

Catalyst No. 6 was prepared in essentially the same manner as that described above for Catalyst No. 4 of Example I with the exception that Catalyst No. 6 was calcined at a much lower temperature. Catalyst No. 6 was heated stepwise at 200° C. for 1.5 hours, then at 300° C. for 1.5 hours. Like catalyst No. 4 of Example I, Catalyst No. 6 of the instant example contained 4.68 weight percent nickel, 9.5 weight percent rare earths and 0.63 weight percent sodium.

Catalyst No. 7 was also prepared from a type X crystalline zeolite material. Catalyst No. 7 was exchanged with a solution of ammonium chloride, the mixture of rare earth chlorides described above and nickel chloride hexahydrate in a manner substantially the same as that utilized for the preparation of catalyst No. 4 described above with the exception that the amount of nickel chloride in the cation exchange solution was one-half that utilized for the preparation of Catalysts No. 4 and No. 6. Catalyst No. 7 was calcined in essentially the same manner as that described above for Catalyst No. 6 of the instant example. Based on extensive experience with similar catalysts, the estimated values for the sodium, rare earths and nickel content for catalyst No. 7 were 0.7, 10, and 3.2 weight percent respectively.

Both catalysts Nos. 6 and 7 were calcined after charging suitable portions, i.e. 18.0 g (20 mL) and 20 g (20 mL) respectively, of said catalysts to the hydroalkylation reactor prior to the hydroalkylation runs.

TABLE II

| Run No. | Catalyst No. | Temp. °C. | Benzene LHSV | Benzene Conv. % | Selectivity, Wt. % | | | | | Wt. Ratio CHB/CH |
|---|---|---|---|---|---|---|---|---|---|---|
| | | | | | CH[a] | C$_{12}$H$_{22}$[b] | MCPB[c] | CHB[d] | Heavies[e] | |
| 1 | 1 | 200 | 9 | 10.6 | 97 | tr. | tr. | 2.8 | n.a.[f] | 0.03 |
| 2 | 2 | 275 | 10 | tr. | —[g] | — | — | — | — | — |
| 3 | 3 | 280 | 5 | tr. | — | — | — | — | — | — |
| 4 | 4 | 265 | 5.5 | 0.4 | 75 | tr. | tr. | 25.0 | n.a. | 0.33 |
| 5 | 5 | 213 | 5 | 4.0 | 40.0 | tr. | tr. | 54.5 | n.a. | 1.50 |

[a] CH = Cyclohexane.
[b] C$_{12}$H$_{22}$ = Compounds of the indicated general formula including bicyclohexyl.
[c] MCPB = Methylcyclopentylbenzene.
[d] CHB = Cyclohexylbenzene.
[e] Heavies = Mixture of compounds greater than C$_{12}$H$_{22}$.
[f] n.a. = No analysis made.
[g] a dash (—) indicates benzene conversion was too low for meaningful analysis results to be obtained.

As shown in runs 1, 4 and 5 some benzene was converted to cyclohexylbenzene. In run 1 the weight ratio of CHB to CH was very low. in run 4 the CHB/CH weight ratio was low with relatively low LHSV and very poor percent conversion. Run 5 produced the highest CHB/CH ratio of runs 1 through 5, but percent conversion and LHSV were relatively low.

EXAMPLE II

Two catalysts were prepared for use in benzene hydroalkylation runs according to the instant invention.

Catalysts Nos. 6 and 7 were utilized in benzene hydroalkylation runs utilizing a continuous reaction system such as that described in Example I above. Prior to the initial introduction of benzene feed the catalysts were prereduced at about 300° C. under 3,450 kPa hydrogen pressure at a flow rate of 0.32 L/min. for about 2 hours. During ech benzene hydroalkylation run, the hydrogen pressure was maintained at 3,450 kPa (500 psig). The water concentration in the benzene feed was believed to be between 25 and 100 ppm. Other reaction conditions and the results obtained in the hydroalkylation runs are shown below in Table III.

TABLE III

| Run No. | Catalyst No. | Temp. °C. | Benzene LHSV | Benzene Conv. % | Selectivity, Wt. % | | | | | Wt. Ratio CHB/CH |
|---|---|---|---|---|---|---|---|---|---|---|
| | | | | | CH | C$_{12}$H$_{22}$ | MCPB | CHB | Heavies | |
| 6 | 6 | 188 | 15 | 13.4 | 42.5 | 1.12 | 1.12 | 45.4 | n.a. | 1.20 |
| 7[a] | 6 | 192 | 9 | 12.7 | 19.0 | 0.47 | 2.91 | 70.8 | 6.9 | 3.70 |
| 8[b] | 6 | 194 | 5.5 | 16.3 | 9.8 | 0.74 | 2.08 | 74.2 | 12.9 | 7.5 |
| 9 | 7 | 222 | 12 | 22.4 | 32.2 | 0.67 | 1.56 | 57.8 | n.a. | 2.00 |

TABLE III-continued

| Run No. | Catalyst No. | Temp. °C. | Benzene LHSV | Conv. % | Selectivity, Wt. % CH | $C_{12}H_{22}$ | MCPB | CHB | Heavies | Wt. Ratio CHB/CH |
|---|---|---|---|---|---|---|---|---|---|---|
| 10[c] | 7 | 166 | 10 | 6.2 | 21.4 | 0.64 | 2.10 | 68.4 | n.a. | 3.50 |

[a]Sampled after catalyst had been exposed to feed stream containing 100 ppm $CCl_4$ for 40 min. at benzene LHSV of 5.
[b]Sampled after catalyst had been regenerated by burning off in air at 480° C. for 3 hours and while feed contained 20 ppm $CCl_4$.
[c]Sampled after catalyst had been exposed to feed containing 100 ppm $CCl_4$ for about 2.7 hours at a feed rate of about 6 LHSV.

Runs 6 through 10 demonstrate the operability of the invention under the conditions employed. Run 6 produced the lowest CHB/CH weight ratio under the conditions employed but this run was carried out at the highest LHSV. Run 7 shows over a threefold improvement in CHB/CH weight ratio as compared to run 6 with only a slight drop in conversion but at a lower LHSV. As indicated in Table III footnote (a), the catalyst in run 7 was treated with a halide source ($CCl_4$) prior to sampling.

Run 8 produced the best CHB/CH weight ratio under the conditions employed. In this run the percentage conversion was higher than in either Run 6 to 7, but the LHSV was the lowest. The catalyst in Run 8 had been regenerated in air at 480° C. and also treated with a halide source.

Comparison of Runs 9 and 10 again demonstrates the increase in conversion to CHB when the catalyst is treated with a halide source. Run 10 also showed a reduction in percent conversion and LHSV as compared to Run 9.

EXAMPLE III

Two other catalysts were prepared which utilized a type Y crystalline zeolite material as the support. These catalysts utilized a commercially available type Y crystalline zeolite material identified as SK-40 of about 10-14 mesh from Linde Division of Union Carbide Corporation.

Catalyst No. 8 was prepared by charging 250 grams of the type Y crystalline zeolite described above to the cation exchange reactor followed by the charging of a solution of 400 grams of ammonium chloride, 200 grams of nickel chloride hexahydrate in 4 liters of distilled water in essentially the same manner as that previously described. The temperature in the cation exchange zone was about 100° C. After the solution had been passed over a crystalline zeolite bed, the material was cooled, filtered and washed six times with 350 mL portions of water and then allowed to dry in air overnight. Catalyst No. 8 contained 1.8% nickel by weight and 1.4 weight percent sodium. Catalyst No. 8 was calcined and prereduced in the hydroalkylation reaction vessel. The hydroalkylation reactor was charged with 20 mL (13.5 grams) of the catalyst which was then heated for 1.5 hours at 200° C. in flowing air with an increase in the temperature to 300° C. for 1.5 hours followed by a purge with nitrogen and then a reduction under hydrogen at 0.32 liters per minute and at 300° C. for 2 hours at 3,450 kPa hydrogen pressure. It will be noted that catalyst No. 8 does not contain rare earths and thus is a control catalyst according to the instant invention though it was calcined under the favorable conditions disclosed for the catalysts of this invention.

Catalyst No. 9 made according to the instant invention was also prepared by charging 250 grams of the type Y crystalline zeolite described above to the cation exchange reactor. A solution of 400 grams of ammonium chloride, 100 grams of the mixture of rare earth chlorides and 200 grams of nickel chloride hexahydrate in 4 liters of distilled water was passed through the crystalline zeolite at about 0.25 LHSV and at about 100° C. The cation-exchanged zeolite material was filtered and washed six times with 350 mL portions of water and allowed to dry in air. Catalyst No. 9 contained 1.33 weight percent nickel, 1.56 weight percent sodium and an estimated 11% rare earths. Catalyst No. 9 was also calcined and prereduced in the hydroalkylation reactor in essentially the same manner as catalyst No. 8. Thus, the reactor was charged with 20 mL (14.0 grams) of catalyst No. 9 and the material heated for 1.5 hours at 200° in flowing air followed by an increase in temperature to 300° C. for 1.5 hours then purged with nitrogen and finally reduced with hydrogen (0.32 liters per minute at 3,450 kPa pressure) at 300° C. for 2 hours.

Catalyst Nos. 8 and 9 were utilized in benzene hydroalkylation runs in the continuous reaction apparatus described earlier. Prior to initial introduction of benzene feed, the catalysts were prereduced using essentially the same conditions described in Example II for the prereduction of catalysts Nos. 6 and 7. During each benzene hydroalkylation run, the hydrogen pressure was maintained at 3,450 kPa (500 psig) and at a flow rate of 0.32 liters per minute of hydrogen. The water content of the benzene feed was believed to be between 25 and 100 ppm. Other reaction conditions and the results obtained in the hydroalkylation runs are shown below in Table IV.

TABLE IV

| Run No. | Catalyst No. | Temp. °C. | Benzene LHSV | Conv. % | Selectivity, Wt. % CH | $C_{12}H_{22}$ | MCPB | CHB | Heavies | Wt. Ratio CHB/CH |
|---|---|---|---|---|---|---|---|---|---|---|
| 11 | 8 | 206 | 12.5 | 5.0 | 10.5 | n.a. | 9.52 | 67.4 | n.a. | 7.6 |
| 12 | 9 | 210 | 10.5 | 16.8 | 10.7 | 0.53 | 3.57 | 74.4 | 10.5 | 6.9 |
| 13[a] | 9 | 206 | 15 | 10.7 | 11.2 | 0.56 | 4.30 | 84.1 | n.a. | 7.5 |
| 14[b] | 9 | 185 | 5.5 | 6.7 | 6.5 | 0.45 | 2.38 | 77.6 | 11.5 | 11.8 |

[a]Sampled after catalyst had been exposed to feed stream containing 100 ppm of $CCl_4$ for about 1 hr. at a feed LHSV of 5.
[b]Sampled after catalyst had been regenerated by burning off in air at 480° C. for 3 hrs.

Runs 12 through 14 demonstrate the operability of the invention under the conditions employed. A comparison of Runs 12, 13 and 14 shows the progressive increase in selectivity to cyclohexylbenzene of catalyst of the present invention initially, after exposure to a halide source, and subsequently after regeneration.

An overall evaluation of the results of the runs in Examples I, II and III indicates that the catalysts of the instant invention show good activity and selectivity in the hydroalkylation of benzene to cyclohexylbenzene. The results also show that addition of a halide source such as $CCl_4$ to the reaction system improves the selectivity with some decrease in activity. Comparison of Run No. 4 with Run No. 6 also clearly shows the dependence of catalyst activity and selectivity on calcination conditions as taught in the instant invention.

What is claimed is:

1. In a process comprising contacting an aromatic hydrocarbon feedstock under hydroalkylation conditions with a catalyst consisting essentially of a calcined, acidic, nickel and rare-earth exchanged crystalline zeolite, to produce a cycloalkyl aromatic product, the improvement comprising employing a catalyst which was calcined at a temperature which did not exceed 400° C.

2. A process as in claim 1 wherein the hydroalkylation conditions include the presence of hydrogen, a pressure within the range of about 690 to about 13,800 kilopascals and a temperature within the range of from about 100° to about 250° C.

3. A process as in claim 1 wherein the hydroalkylation conditions include the presence of water at a concentration in the feedstock of at least 5 parts per million by weight and sufficient to mitigate catalyst deactivation.

4. A process as in claim 3 wherein the catalyst has been calcined at a temperature within the range of from about 150° about 400° C. for a period of time in the range of from about 1 to about 24 hours.

5. A process as in claim 4 wherein the hydroalkylation conditions include the presence of a halide source in an amount sufficient to improve the selectivity of the catalyst to produce a cycloalkyl aromatic hydrocarbon.

6. A process as in claim 1 wherein the hydroalkylation conditions include the presence of water at a concentration in the feedstock in the range of from about 5 to about 500 parts per million by weight.

7. A process as in claim 6 wherein the catalyst has been calcined at a temperature within the range of from about 175° to about 325° C. for a period of time within the range of from about 2 to about 5 hours.

8. A process as in claim 7 wherein the hydroalkylation conditions include the presence of a halide source in an amount within the range of from about 0.1 to about 100 milligrams of halide ion per gram of catalyst.

9. A process in accordance with claim 1 wherein the catalyst contains alkali metal within the range of about 0.01 to about 2 percent by weight;
wherein the catalyst contains at least one rare earth metal within the range of from about 2 to about 25 percent by weight; and
wherein the catalyst contains nickel metal within the range of from about 0.1 to about 20 percent by weight.

10. A process in accordance with claim 1 wherein the crystalline zeolite has a pore diameter within the range of from about 7 to about 12 angstroms;
wherein the zeolite is exchanged with a rare-earth metal compound selected from the group consisting of nitrates, bromides, acetates, chlorides, iodides, sulfates and mixtures thereof;
wherein the zeolite is exchanged with a nickel compound selected from the group consisting of nitrates, bromides, acetates, chlorides, iodides, sulfates and mixtures thereof; and
wherein the rare earth metal exchanged into the zeolite is selected from the group consisting of cerium, lanthanum, praseodymium, neodymium, samarium, europium, gadolinium, terbium, dysprosium, holmium, erbium, thulium, ytterbium, lutetium and mixtures of any two or more thereof.

11. A process in accordance with claim 1 wherein the catalyst contains alkali metal within the range of about 0.05 to about 1 percent by weight;
wherein the catalyst contains at least one rare earth metal within the range of from about 5 to about 20 percent by weight; and
wherein the catalyst contains nickel metal within the range of from about 1 to about 10 percent by weight.

12. A process in accordance with claim 1 wherein the catalyst is treated with hydrogen prior to being contacted with the aromatic hydrocarbon.

13. A process in accordance with claim 1 wherein the aromatic hydrocarbon is contacted with said catalyst at a liuid hourly space velocity within a range of about 1 to about 100, wherein the hydrogen is contacted with the catalyst at a hydrogen feed rate within a range of about 0.1 to about 10 moles per hour of hydrogen per mole of aromatic hydrocarbon at a hydrogen pressure within a range of about 690 to about 13,800 kilopascals (100 to 2000 psig), and a temperature within a range of about 100 to about 250° C.

14. A process in accordance with claim 1 wherein the aromatic hydrocarbon is contacted with said catalyst at a liquid hourly space velocity within a range of about 5 to about 25, wherein the hydrogen is contacted with the catalyst at a hydrogen feed rate within a range of about 0.2 to about 1 mole of hydrogen per mole of aromatic hydrocarbon per hour at a hydrogen pressure within a range of about 1380 to about 6900 kilopascals (200 to 1000 psig), and a temperature within a range of about 140 to about 200° C.

15. A process as in claim 1 wherein the hydroalkylation conditions include the presence of water in the feedstock at a concentration of from about 10 about 100 parts per million by weight.

16. A process as in claim 1 wherein the hydroalkylation conditions include the presence of water in the feedstock at a concentration of from about 20 to about 50 parts per million by weight.

17. A process in accordance with claim 1 wherein the hydroalkylation conditions include the presence of a halide source in an amount within a range of from about 0.5 to 10 milligrams of halide ion per gram of said catalyst.

18. A process in accordance with claim 8 wherein the halide source is selected from the group consisting of fluorine, bromine, chlorine, iodine, carbon tetrachloride, carbon tetraiodide, tetrachloroethylene, chloroform, bromoform, dichloromethane, dibromomethane, difluoromethane, chloromethane, bromomethane, 1,4-dichlorobutane, 1,4-dibromobutane, 1-chlorobutane, 1-fluorobutane, 1-bromobutane, 1,2-dichloroethane, 1,2-dibromoethane, 2-chloropropane, 2-bromopropane, acetyl iodide, acetyl achloride, acetyl bromide, bromochloromethane, 1-bromo-4-chlorobutane, 1,2-dichloroethylene, 1,2-dibromoethylene and mixtures of any two or more thereof.

19. A process in accordance with claim 17 wherein the halide source is selected from the group consisting of bromides and chlorides.

20. A process as in claim 17 wherein the aromatic hydrocarbon feedstock contains the halide source.

21. A process in accordance with claim 20 wherein the halide source is carbon tetrachloride.

22. A process in accordance with claim 1 wherein the crystalline zeolite is selected from the group consisting of Type L, Type X and Type Y zeolites; and
- the source of the nickel metal exchanged into crystalline zeolite is nickel chloride hexahydrate and the source of the at least one rare earth metal exchanged into the crystalline zeolite is a mixture of the chlorides of at least lanthanum, cerium, praseodymium, neodymium, samarium and gadolinium.

* * * * *